United States Patent [19]

Boniface et al.

[11] Patent Number: 5,585,116

[45] Date of Patent: Dec. 17, 1996

[54] METHOD OF MANUFACTURE OF A MATERIAL FOR OSTEOPLASTY FROM A NATURAL BONE TISSUE AND MATERIAL OBTAINED THEREBY

[75] Inventors: Robert Boniface, Vallangoujard; Michel Faurie, Veyre-Monton; Pablo Goldschmidt, Paris; Jean-Pierre Lontrade, Clermont-Ferrand; Jacques Luyckx, Ceyrat, all of France

[73] Assignee: OST-Developpment, France

[21] Appl. No.: 383,654

[22] Filed: Feb. 3, 1995

Related U.S. Application Data

[63] Continuation of Ser. No. 858,985, filed as PCT/FR90/00842, Nov. 22, 1990, published as WO91/07194, May 30, 1991, abandoned.

[30] Foreign Application Priority Data

Nov. 22, 1989 [FR] France ..................... 89 15363

[51] Int. Cl.$^6$ ............... A61K 35/32; A61F 31/00; A61F 2/28; C12N 5/00
[52] U.S. Cl. .............. 424/549; 435/240.2; 514/588; 623/16; 424/422
[58] Field of Search ............... 435/1.1, 240.2; 514/588; 623/16; 424/549

[56] References Cited

U.S. PATENT DOCUMENTS

| | | | |
|---|---|---|---|
| 3,318,774 | 5/1967 | Dingwall et al. | 167/74 |
| 4,434,094 | 2/1984 | Seyedin et al. | 424/549 |
| 4,440,750 | 4/1984 | Glowacki et al. | 424/95 |
| 4,485,097 | 11/1984 | Bell | 424/549 |
| 4,678,470 | 7/1987 | Nashef et al. | 623/16 |
| 5,290,558 | 3/1994 | O'Leary et al. | 424/422 |
| 5,336,616 | 8/1994 | Livesey et al. | 435/240.2 |
| 5,439,684 | 8/1995 | Prewett et al. | 424/422 |
| 5,484,601 | 1/1996 | O'Leary et al. | 424/422 |

FOREIGN PATENT DOCUMENTS 2175807  12/1986  United Kingdom.

OTHER PUBLICATIONS

Urist et al., "Bone Morphogenesis in Implants of Insoluble Bone Gelatin," Proc. Nat. Acad. Sci. USA, vol. 70, No. 12, Part I, pp. 3511–3515, Dec.–1973.

Primary Examiner—Michael G. Wityshyn
Assistant Examiner—Kristin Larson
Attorney, Agent, or Firm—Millen, White, Zelano & Branigan

[57] ABSTRACT

Osteoplasty material substantially devoid of antigenic proteins, wherein the material contains a natural bone structure in which non-denatured type I collagen is integrated, is prepared by selective extraction of bone tissue of human or animal origin. The selective extractant is an aqueous solution of 2–10 molar urea, and the extraction step is conducted at preferably 10°–30° C.

24 Claims, No Drawings

METHOD OF MANUFACTURE OF A MATERIAL FOR OSTEOPLASTY FROM A NATURAL BONE TISSUE AND MATERIAL OBTAINED THEREBY

This application is a continuation, of application Ser. No. 07/858,985, filed as PCT/FR90/00842, Nov. 22, 1990, published as WO91/07194, May 30, 1991, now abandoned.

BACKGROUND OF THE INVENTION

The present invention relates to material intended for osteoplasty as well as to a method of manufacture for obtaining said material from bone tissue of human or animal origin. The essential object of the invention is to provide surgeons with bone substitute material which is biocompatible, non-antigenic, osteocompatible, osteointegrable, etc.

This invention is intended to produce grafts or transplants which can be recut to the shape of the bone defect, thus enabling surgeons to employ a graft of this type as an alternative either to an autograft which accordingly makes it possible to dispense with the second operating site or to a homograft on account of the drawbacks and dangers involved.

This material is advantageously improved with respect to those of the prior art by virtue of its method of manufacture which is particularly well suited to the formation of a bone graft in reparative, traumatological, orthopedic, maxillofacial or mandibular surgery as well as in dental or veterinary surgery and, in a general sense, whenever a bone site calls for the use of a graft.

The use of replacement or substitute bone tissue is not a new technique. The first scientific publications date back to the vicinity of 1800 and have greatly increased in number since that time. They relate to homografts and xenografts containing relative proportions of minerals and proteins which may vary according to the methods adopted. A parallel development which has taken place subsequently to the initial use of these bone substitutes of human and animal origin has consisted in the use of grafts of a mineral nature such as corals, hydroxyapatites, ceramics or of synthetic nature such as biodegradable polymer materials.

At the present time, research efforts undertaken in this field are being directed to the use of materials which are closer to bones both in structure and in composition, and specifically to human bone, in order to facilitate integration of the bone graft. This involves recognition by the body of the new structure and colonization in accordance with the so-called "creeping substitution" mechanism.

Bone is a living tissue which undergoes a never-ending process of reorganization involving simultaneous destruction and reconstruction of bone material. In the normal process, but also when foreign material is implanted, the osteoclasts resorb the old tissue, thus leaving a gap in which the osteoblasts generate the new tissue. A balance is always maintained between the quantities of resorbed bone and the quantities of newly formed bone. It appears that this phenomenon is likely to take place with greater ease as the implanted structure bears a closer resemblance to that of normal bone.

Thus it is now preferred to prepare bone substitution materials from natural bone tissues which are preferably of animal origin for ethical and practical reasons.

Generally speaking, it is known that partial demineralization facilitates integration of a bone graft. This is accordingly followed by different complementary steps which are intended either to deproteinize the bone completely or to act on the nature of the proteins which then remain linked within the bone matrix or else to increase this proportion of proteins.

In the prior art, there may be cited in particular U.S. Pat. No. 4,394,370 which proposes to fuse into a spongy mass by means of a glutaraldehyde binder which has a cross-linking effect, a mixture consisting of powdered demineralized bone of human origin and of reconstituted collagen powder.

U.S. Pat. No. 4,743,259 combines demineralization by hydrochloric acid with enrichment with proteins carried out on a first fraction of demineralized bone by means of proteins extracted from a second fraction by guanidine.

Moreover, French patent Applications No. 2,582,517 and No. 2,582,518 propose to treat fragments of bones taken from animals, more especially from cattle, by partial demineralization and tanning by means of glutaraldehyde. The bone elements to be implanted by the surgeon are cut to the appropriate shape from an ox bone which has previously been subjected to a treatment comprising a delipidation or degreasing step with an organic solvent such as ethanol, a demineralization step by means of a calcium extraction agent such as hydrochloric acid, and a step which involves tanning with glutaraldehyde, as well as various washing operations.

It is apparent from the specifications of the patents cited in the foregoing that the above-mentioned tanning process has a beneficial effect on the properties of treated bone insofar as it facilitates cross-linking of the macromolecular chains. However, it has now been found that, on the contrary and in contrast to the suggestions made in the prior art, the treatment with glutaraldehyde does not result in any appreciable reduction of the immunogenic properties and, in addition, reinhabitation of the implanted bone is not promoted as should preferably be the case in order to ensure integration of the bone graft. Furthermore, chemical compounds such as glutaraldehyde have the disadvantage of being biologically toxic.

When the present invention was conceived, a condition observed at the outset was that, in order to achieve good integration of the bone graft, it is essential to maintain the collagen in the bone material while keeping it in the specific form which it has in natural bone (mainly in the form of type I collagen) and at the same time maintaining the microscopic appearance of the bone, as well as to preserve the spatial bone structure which is intended to support a subsequent colonization of cells. It has also been observed that the treatments of the prior art have substantially the same effect on the collagen of the bone as on the other proteins which they are intended to remove or to denature in order to eliminate their antigenicity.

SUMMARY OF THE INVENTION

The invention is therefore directed to a method of treatment of bone tissue of human or animal origin which results in bone substitute material characterized by the preservation of the original bone structure, which integrates non-denatured type I collagen but which is freed from the antigenic proteins. The method results in the surprising discovery that it is possible to carry out on natural bone tissues a step of selective extraction of the antigenic proteins while preserving the structural collagen.

In more specific terms, the method in accordance with the invention essentially involves at least one step of selective extraction and/or denaturation of the non-collagenous structural proteins, this step being carried out by means of a selective extraction agent having a base of urea. Within the field of the present invention, urea is advantageously employed in the form of an aqueous solution at a concentration which is usually within the range of 2 to 10M and preferably 5 to 8M. The temperature is ordinary temperature or may generally have a value within the range of 15° to 30° C.

The analytical follow-up of the method in accordance with the invention involving utilization of urea or of a similar extraction agent shows that the reactions thus produced tend to break the macromolecular chains of the undesirable proteins which remain in the structure of the original bone after carrying out conventional delipidation operations whereas the structural collagen is practically not attacked. The material obtained is distinguished not only by its properties relating to applicability but also by its characteristics of composition and structure from all materials known up to the present time for the same application, in particular those which involved reincorporation of skin collagen in a demineralized bone skeleton or those directed to restructuration of the collagen since this appears to lead to a system of crystallization which is different from natural crystallization.

In a preferred mode of execution of the invention, the method does not include preliminary operations of partial demineralization of the delipidated bone. However, the known techniques of demineralization may also be used at this stage.

After the essential extraction step in accordance with the invention, the method advantageously includes a subsequent washing step which is conventional per se and serves to remove the proteins from the bone material during treatment, selectively with respect to the collagen having a non-denatured structure. In the practical application of the method in accordance with the invention, this washing step is preferably carried out at a temperature within the range of 30° C. to 60° C. and preferably of the order of 45° C. to 55° C. An advantageous compromise is thus achieved between the desirable removal of proteins and preservation of the collagen in its untanned form, which has a beneficial effect on the final properties of the material to be implanted in bone surgery.

In accordance with secondary features of the invention, the method may involve a repetition of the essential step of selecetive extraction by urea, advantageously combined with another agent which is capable of breaking the disulfide bridges such as mercaptoethanol, this step being followed each time by a suitable washing step.

Moreover, the method as a whole may also include a number of different steps which are conventional per se and especially a step of extraction by an ionic solvent consisting in particular of an aqueous solution of a salt such as sodium chloride.

It will be noted that, in the practical application of the method according to the invention, the extraction agents employed can be readily selected from compounds which do not have any toxic effect on the human body, which is not the case, for example, with glutaraldehyde employed in the prior art.

In its preferred embodiments, the method in accordance with the invention results in bone material in which the usual analytical techniques make it possible to detect the presence of structural collagen in a proportion which is advantageously within the range of 20 to 40% and preferably of the order of 25 to 35%.

It is therefore clear that, on completion of the treatment, the material obtained does not contain all the original collagen which is known to represent approximately 90% of the organic material of the degreased dry bone, approximately 95% of this proportion being made up of type I collagen, characterized by a molecule of tropocollagen formed by three polypeptide chains arranged in a helix, comprising two type I alpha-1 chains and one type I alpha-2 chain, and approximately 5% of type III collagen, which comprises three identical alpha-1 chains. Nevertheless, only the collagen which is readily extractable at the same time as other proteins is removed during conventional operations consisting of preliminary delipidation and demineralization if necessary, whereas the greater part of the structural collagen remains unattacked when the other proteins which had not previously been removed are denatured by urea, these products being essentially constituted by proteoglycans or antigenic glycoproteins.

However, the properties of the material obtained by the method in accordance with the invention, especially its capacity for osteointegration but also its mechanical properties and its formability appear to be precisely related to the presence of the original collagen which is integrated in the microporous structure and mainly consists of type I collagen. It is also worthy of note that the invention usually leads to relative enrichment of the collagen in type I collagen up to a proportion for example of 97% of type I collagen and 3% of type III collagen.

This result is observed in the material obtained in accordance with the invention by means of known techniques of characterization of types of collagen which consist for example either in observing the collagen by immunofluorescence after having caused it to react with anti-collagen (type I) antibodies or in subjecting it to the action of cyanogen bromide in order to obtain a mixture of characterizable peptides which are separated as a function of their molecular weights and analyzed by electrophoresis.

In the majority of instances, the material in accordance with the invention and obtained in accordance with the method in which recourse is had to preliminary partial demineralization has a composition within the ranges indicated hereunder (in % by weight):

| Water | 2–10 or less than 10 |
|---|---|
| Lipids | 1–15 or <15 |
| Ash | 40–65 |
| Calcium | 10–25 |
| Phosphorus | 5–20 |
| Ca/P | 1–2.2 |
| Proteins | 30–45 |
| Collagen | 20–40 |

In the preferred case in which the method does not involve preliminary partial demineralization, the material advantageously has a composition within the ranges indicated hereunder:

| Water | <10 |
|---|---|
| Lipids | <2, namely 0, 1–2 |
| Minerals | 50–70 |
| Calcium | 20–30 |
| Phosphorus | 10–17 |
| Ca/P | 1.6–2.2 |
| Proteins | 25–35 |
| Collagen | 20–30 |

The invention will now be described in greater detail within the scope of particular examples of application of the

EXAMPLE I

Preparation of the material in the form of blocks.

The starting material consists of blocks of bone cut-out beforehand from epiphyses or diaphyses of ox bones freshly obtained from the slaughterhouse. Depending on the intended use, preference may be given to spongy bone (epiphysis) or to cortical bone (diaphysis). In the case under consideration, in which good compressive strength is desired, it is preferable to carry out transverse cuts of epiphyses at right angles to the trabecular framework.

These blocks are first treated in accordance with a conventional step of delipidation of the bone tissue with a mixture of chloroform and methanol or of ethanol and dichloromethane, the volume of delipidating mixture being approximately 10 volumes for 1 part of initial fresh bone (10 l/kg). This step permits extraction of free lipids, fatty acids, lipoproteins, associated with the bone stroma. In the example under consideration, this step is carried out as follows: 400 g of blocks of bone are treated with a mixture of 4 l of chloroform and methanol (⅔–⅓) at a temperature of 4° C. over a period of 24 hours with agitation.

Throughout the remainder of the operations and unless otherwise stated, this proportion of 10 volumes for one part of initial bone will be maintained.

In an example Ia (but not in an example Ib), the blocks are then subjected to a demineralization step performed by contacting them with 0.6M hydrochloric acid at 4° C. over a period of 6 hours. This step is conventional and the operating conditions can be varied in accordance with the description given for example in French Patent No. 2,582,517, by employing a hydrochloric acid solution having a molar concentration within the range of 0.1M to 1M, or another mineral or carboxylic acid and/or an organic agent which is capable of complexing the calcium of bone such as ethylenediaminetetraacetic acid.

By way of alternative, it is also possible to increase the time of contact with HCl, for example to thirty-six hours. Depending on the treatment time, the material obtained will have a greater or lesser degree of hardness adapted to requirements for future use.

During this demineralization step, the ions of hydroxyapatite which forms part of the bone collagen stroma are therefore removed in part, thus making this stroma more accessible for subsequent extractions.

The following step consists of an extraction by contacting with an aqueous solution of sodium chloride: the blocks are treated with 4 l of a 1M sodium chloride solution at a temperature of 4° C., with agitation, over a period of thirty-six hours.

This extraction makes it possible to remove the most soluble or freshly synthesized macromolecular components from the bone material. In the extract are found lipids which had remained after the previous treatments, proteoglycans and collagens. This step makes it possible to avoid denaturation of the collagen stroma while partially extracting a few components before attacking the more resistant matrix components in the following extraction steps.

In Example Ia as in Example Ib, the extraction operation just mentioned immediately precedes the essential step of the invention, in which the bone blocks are put in contact with 4 l of 8M urea at room temperature (20° C.) over a period of six hours.

This step permits extraction of molecules such as proteoglycans and glycoproteins including the structural glycoproteins which are molecules having the highest antigenicity in bone, but without causing excessive denaturation of the conjunctive collagen stroma.

This extraction is completed by a fresh extraction having a similar purpose and carried out by means of a 0.2% solution of mercaptoethanol in 8M urea at room temperature over a period of twenty-four hours.

When both of these two selective extraction steps have been completed, it is found that the non-collagenous glycoprotein elements have been extracted or at least denatured in an effective manner, thus preventing rejection of the material to be grafted as a result of the natural antigenicity of its glycoproteins which are present in the macromolecular composition of the bone tissue stroma.

The different solvents and reagents employed during the preceding operations are then removed by washing with 4 l of distilled water at 55° C. over a period of twenty-four hours.

There then follows a treatment with a 0.4M phosphate buffer solution (pH =7.4) which is carried out with agitation over a period of forty-eight hours at 35° C. This operation is followed by rinsing with 2 l of ethanol at room temperature over a period of twenty-four hours.

Vigorous washing with pure water serves to remove or rather to continue the extraction of lipids, proteoglycans, collagens and glycoproteins. The treatment temperature employed makes it possible to inhibit the enzymatic activities which are present in the tissues, namely those derived from endogenous proteases or exogenous proteases of bacterial origin, for example, as well as other lytic enzymes.

As far as extraction with the phosphate buffer solution is concerned, this operation continues removal of the matrix and/or lipid components which may still be attached to the bone stroma. The extraction process also makes it possible to restore the equilibrium of the bone material in regard to the salts which are present.

Finally, washing in an alcohol bath permits final and complete extraction of the compounds which are still weakly associated with the collagen stroma, in particular residual lipids, but primarily facilitates the subsequent isolation operation.

In fact, the bone fragments treated in accordance with the invention with a view to obtaining osteoplasty material are finally drip-dried, rinsed with ethyl alcohol and dried in a ventilated oven. They can also be frozen and/or lyophylized in order to be stored in readiness for use. Individual parts can readily be formed so as to obtain the shapes which are suitable for use. Thus the material can be provided in the form of parallelepipedal blocks having different dimensions, pyramidal frustums, lamellae, centro-medullary end-caps, disks, and so on. The final forms are then packaged and sterilized by ionizing radiation.

EXAMPLE II

Analytical Study.

The material finally obtained was subjected to microscopic, biochemical and chemical examinations.

a) Examination in optical microscopy, optical and polarized light. This examination shows that the structure of the bone tissue is preserved. It is seen especially that the characteristic appearance of the trabecular framework of the spongy tissue again has its characteristic appearance. It is established in particular that the collagen is present in its original arrangement, thus making a very marked difference between the material in accordance with the invention and any products of the prior art which might result from an addition of exogenous collagen on any support.

b) Examination in fluorescence microscopy. This examination permits characterization of the specific lamellar structure which is very close to that of natural bone. Characterization of the type I collagen was achieved by making use of specific type-1 anti-collagen antibodies.

c) In biochemistry, typing with cyanogen bromide confirms that the collagen is in fact type I collagen. It is found that alpha-1 CB7 and alpha-1 CB8 peptides are present. The presence of alpha-1 CB6 peptides confirms the cross-linkage of the chains and therefore the partial preservation of the spatial structure. The presence of alpha CB3 is also noted.

These results, compared with the reference substances, reveal the presence of a characterized type I collagen.

d) In chemistry, a mean value of the analyses performed on four batches resulting from the application of the method in accordance with Example I gives the following results expressed as a percentage by weight with respect to the total weight of dry materials:

Example Ia:

| Quantity determination | Mean value % | Extreme values |
| --- | --- | --- |
| Loss on drying | 6.8 | 6.3–7.3 |
| Lipids | 10.8 | 7.4–14.0 |
| Ash | 48.4 | 44.6–53 |
| Calcium | 16.8 | 15.5–18.0 |
| Phosphorus | 11.5 | 8.8–13.4 |
| Ca/P | 1.49 | 1.22–1.86 |
| Proteins | 36.8 | 35.4–38.5 |
| Collagen | 30.2 | 29.5–30.7 |

Example Ib (analyses of six batches):

| Quantity determination | Mean value % | Extreme values |
| --- | --- | --- |
| Water | 8.9 | 7.3–9.7 |
| Lipids | <0.3 | <0.3 |
| Ash | 61.7 | 60–65 |
| Calcium | 22.64 | 21.5–25.3 |
| Phosphorus | 11.5 | 10.3–12.4 |
| Ca/P | 1.97 | 1.7–2.22 |
| Proteins | 29.6 | 28–31 |
| Collagen | 27.3 | 25.6–29.3 |

The mean apparent density of the product varies between 0.32 and 0.57 g/cm$^3$ depending on the samples, about a mean value of 0.39 g/cm$^3$.

EXAMPLE IIIa preparation of material in powdered form.

Fragments taken from ox bones (without any need for concern as to the orientation of cutting planes) are treated as described in Example I. They are then reduced to powder which can be used directly as it stands.

EXAMPLE IIIb

Preparation of molded material.

By way of alternative, powders having different particle sizes are employed at the outset to mold parts to the desired shapes by means of a binder which can advantageously be of biological origin but may also be a biodegradable synthetic polymer according to its intended use.

In the particular case of the present example, material having the function of a binder and formed so as to permit revascularisation (such as a bioresorbable polymer of the polylactic resin group) was employed in a proportion of 1 to 10 parts to 1 part of bone powder. It would also be possible to employ fibrin in a proportion of 1 or 2 parts to 100 parts of bone. The particle size of the powders varies from 1000 to 250 μ.

The final formed parts are then sterilized by irradiation and sealed in a sterile package.

EXAMPLE IV

Variants of the method.

Ox bones are treated as in Example I except for the fact that final washing with alcohol is preceded (before or after washing with distilled water) by a further step of delipidation by a mixture of chloroform and methanol or a mixture of ethanol and dichloromethane.

This step permits final and complete delipidation of the conjunctive bone stroma and therefore permits removal of the lipidic substances, fatty acids or lipoproteins which still remain attached to the bone stroma. By carrying out this extreme delipidation, it is thus possible for example to obtain under better conditions a bone powder in accordance with Example III having a composition of residual lipids which is advantageously reduced to a proportion of less than 5%.

Similarly, it may be advisable to add two additional delipidation steps, thus making it possible to obtain a product containing a wholly negligible proportion of residual lipids, namely of the order of 1% or less than 1%.

As can readily be understood, the relative percentages of the other constituents are modified under these conditions.

Changes have also been made in the conditions of the different treatment steps, especially in concentrations, contacting times and temperatures, by applying them to blocks in which the three dimensions varied between 8 and 30 centimeters. The limits of the conditions adopted were as follows:

Suppression of the step involving extraction by an ionic solvent, which in other cases is performed by means of a 0.5 to 2 M solution of NaCl at a temperature of 2° to 5° C. over a period of twelve to thirty-six hours.

Aqueous solution of urea having a concentration within the range of 5 to 10M.

Aqueous solution of mercaptoethanol in urea containing 0.1 to 0.5 volume % of mercaptoethanol.

Time of selective extraction by this solution, within the range of twelve to thirty-six hours at room temperature.

Satisfactory materials for osteoplasty have thus been obtained, the results of analysis of these materials being within the following ranges (% by weight):

| Ash | 40 to 70, especially 60 to 65% |
| --- | --- |
| Lipids | 0.5 to 2% |
| Loss on drying | 7 to 10% |
| Proteins (Kjeldahl) | 25 to 45% |
| Calcium | 10 to 30% (10 to 20 or 20 to 30) |
| Phosphorus | 10 to 17% |
| Ratio Ca/P H | 1 to 2.2 (1 to 1.3 or 1.6 to 2.2) |
| Collagen | 33 to 38% |

(dosage of collagen according to hydroxyproline)

The same results are obtained in the variants of the invention involving the use of a powder as is described in Example III.

EXAMPLE V

Clinical observation on a one-year-old castrated male cat.

This animal had been the victim of an accident (traumatic shock caused by an automobile) which resulted in a comminuted fracture of the right thigh bone at the level of the proximal metaphyseal and trochanteric region. By making use of the osteoplasty material in accordance with the invention, the cat was operated-on eight days after the traumatism by means of the following technique: conventional approach of seat of fracture, insertion of a block prepared in accordance with Example I in the reconstituted trochanteric mass and synthesis by reconstruction of the femoral diaphysis by means of the Perot small-size external fastener (threaded transfixing pins 2 mm in diameter).

The animal was restored to a completely normal walking, running and jumping function. Radiographs taken at intervals of sixty and ninety days showed satisfactory bone reconstruction and incipient union of the graft. This made it possible to avoid the complications of a fracture which could have led to amputation of the limb in the event of non-consolidation.

EXAMPLE VI

German sheepdog.

This animal had been the victim of a road accident which resulted in a comminuted diaphyseal fracture with splinter. Operation of the dog was carried out rapidly and was followed by placement of a heterologous graft prepared from a block of ox bone treated as in Example I. The graft was sculptured in the block so as to obtain a tongue-and-groove assembly at the level of the femoral diaphyseal ends to be joined. Solidification of the osteosynthesis assembly was achieved by apposition of a Perot straight plate and screwing on the femoral diaphysis with a 3.5 mm diameter screw.

The animal recovered its support after only a few days. Radiographic tests carried out at intervals of thirty and sixty days showed stability of the assembly and incipient union of the graft.

EXAMPLE VII

Use of the material in accordance with the invention in powdered form for apical resection on a patient's upper left lateral incisor.

The operation was performed in accordance with a conventional technique, namely semilunar incision with exeresis of the cyst and sterilization of the site with a C02 laser. Placement of the material according to the invention and in powdered form as obtained in accordance with Example III was carried out by mixing it with sterile physiological serum and by compressing it within the sanguinolent osseous geode. The gingival flap was then replaced and sutured and a test radiograph was taken.

It was noted after a period of eight days that excellent cicatrization had begun. After one week, the quality of the radiographic image was much better than those obtained with the other filling materials employed in standard practice. Thus the radioopacity of the material in accordance with the invention is very close to that of human alveolar bone.

At intervals of two weeks and one month, the radiographs confirmed these results. Cicatrization was perfect and no rejection phenomenon had appeared.

From the evidence shown by the radiographic appearance, it may be asserted that "integration" of the powder takes place. In the experience of the practitioner who performed this operation, this is wholly exceptional in comparison with the results observed in the case of the other known filling products which are commercially available.

EXAMPLE VIII

Use of the material in accordance with the invention for restoring two periodontal pockets to a sound condition in a 50-year-old patient.

The operation consisted first in reclining a flap which extended from the upper left central incisor to the second upper left molar, then in sterilizing the bone and root portions of the pockets by deep scaling, curetting and surfacing of roots.

The granulation tissue at the gingival level on the flap and within the pockets was volatilized by means of a CO2 laser, whereupon the periosteum and the pockets were rinsed with physiological serum.

Two blocks prepared in accordance with Example I were employed. These sterile blocks were cut to the required dimensions under strictly sterile conditions. The two blocks were forcibly fitted in position so as to establish an intimate contact and serve as retention means. On completion of this operation, the flap was then replaced and sutured.

Eight days after removal of the surgical bandage, when the stitches had been removed and the operation site had been cleaned, it was observed that certain stitches (two) had failed and that the two blocks were not perfectly covered since they were still slightly visible. However, the cicatrization state was satisfactory and, surprisingly, a neo-gum of the kind which normally develops at the level of the periosteum when this latter has been bared was found to be developing above the blocks. This may accordingly be considered to constitute "recognition" of the material in accordance with the invention by the neogum. This result is confirmed by the radiographic test.

After a period of two weeks, the two blocks of the material in accordance with the invention were entirely covered by the transfer flap and by the neogum at the level of the uncovered zones.

This confirms that, by virtue of its "neutrality" or its structure which is close to that of human alveolar bone, the material in accordance with the invention integrates perfectly and is covered by a neogum as is the case with the periosteum.

The final radiograph taken at the end of one month confirms that the two blocks had perfectly integrated in their site. No rejection phenomenon was observed. Furthermore, the teeth were no longer liable to move and the gingival appearance was restored to normal, which is exceptional in view of the problems arising from postoperative sutures.

We claim:

1. A method for producing an osteoplasty material, comprising
    (a) providing a starting non-demineralized bone tissue of human or animal origin, containing antigenic, non-collagenous structural proteins and structural collagen,
    (b) subjecting said bone tissue to at least one selective extraction of the antigenic proteins with an aqueous selective extraction agent containing urea at a sufficient concentration and a sufficient temperature so as to selectively decompose the antigenic non-collagenous protein structure without attacking type I collagen, and
    (c) recovering an osteoplasty material for bone implants having the natural bone structure of the starting bone tissue and type I collagen integrated therein in non-denatured form.

2. The method of claim 1, wherein the urea is in the form of an aqueous solution at a concentration within the range of 2 to 10M.

3. The method of claim 2, wherein the selective extraction step is conducted at 10°–30° C.

4. The method of claim 2, wherein the concentration of the urea is 5–8 molar.

5. The method of claim 4, wherein the selective extraction step is conducted at 10°–30° C.

6. The method of claim 1, wherein said selective extraction is followed by a further selective extraction with an aqueous solution of urea containing mercaptoethanol in a concentration of 0.1 to 0.5 volume %.

7. The method of claim 1, wherein said selective extraction is preceded by extraction of soluble constituents into an ionic solvent.

8. The method of claim 1, wherein after completion of said selective extraction, at least one washing step which entrains denatured structural glycoproteins is performed.

9. The method of claim 1, wherein said washing step is carried out with distilled water at a temperature within the range of 30° C. to 60° C.

10. The method of claim 9, wherein the washing step is carried out at 45°–55° C.

11. The method of claim 1, wherein the selective extraction is conducted at 10°–30° C.

12. The method of claim 1, wherein, prior to said selective extraction, said starting non-demineralized bone tissue is subjected to a delipidation treatment.

13. The method of claim 12, wherein said selective extraction is followed by a further selective extraction with an aqueous solution of urea containing mercaptoethanol in a concentration of 0.1 to 0.5 volume %.

14. The method of claim 12, wherein said delipidation is carried out by contacting the starting non-demineralized bone tissue with a mixture of chloroform and methanol or a mixture of ethanol and dichloromethane in a proportion of approximately 10 liters to 1 kg of non-demineralized bone tissue.

15. The method of claim 14, wherein said selective extraction is followed by a further selective extraction with an aqueous solution of urea containing mercaptoethanol in a concentration of 0 1 to 0 5 volume %.

16. The method of claim 12, wherein said selective extraction is followed by a further selective extraction with an aqueous solution of urea containing mercaptoethanol in a concentration of 0.1 to 0. 5 volume %.

17. The method of claim 12, wherein said selective extraction is preceded by extraction of the soluble constituents into an ionic solvent.

18. An osteoplasty material obtained by a method in accordance with claim 1, wherein said osteoplasty material preserves the original and natural bone structure in which non-denatured type I collagen is integrated.

19. The osteoplasty material of claim 18, containing structural collagen in a proportion within the range of 20 to 40%.

20. The osteoplasty material of claim 19, wherein the structural collagen present is in a proportion within the range of 25–35%.

21. The osteoplasty material in accordance with claim 18, containing a proportion of lipids lower than 15%, a proportion of proteins within the range of 25 to 45%, a proportion of calcium of 10 to 30%, a proportion of phosphorus of 5 to 20%, and a water content lower than 10%, by dry analysis.

22. The osteoplasty material of claim 21, wherein the ratio calcium/phosphorus is from 1–2.2.

23. The osteoplasty material of claim 18, wherein said osteoplasty material is formed into parallelepipedal blocks, pyramidal frustums, lamellae, centro-medullary end-caps, disks or powder optionally amalgamated by means of a binder of biological origin or of synthetic origin.

24. A method for producing an osteoplasty material, comprising (a) providing a starting non-demineralized bone tissue of human or animal origin containing antigenic, non-collagenous structural proteins and structural collagen, (b) delipidating the non-demineralized bone tissue of (a) to remove free lipids therefrom, (c) subjecting said bone tissue to at least one selective extraction of the antigenic proteins with an aqueous selective extraction agent containing urea at a sufficient concentration and a sufficient temperature to selectively decompose the antigenic non-collagenous protein structure without attacking type I collagen, (d) recovering an osteoplasty material for bone implants having the natural bone structure of the starting bone tissue and type I collagen integrated therein in non-denatured form, and (e) optionally washing and rinsing the osteoplasty material of (d).

* * * * *